United States Patent
Deforge et al.

(10) Patent No.: US 6,280,387 B1
(45) Date of Patent: Aug. 28, 2001

(54) THREE-DIMENSIONAL TISSUE/FLOW ULTRASOUND IMAGING SYSTEM

(75) Inventors: Christian Deforge, Seattle; Dong-Chyuan Liu; Stephen P. Czenszak, both of Mercer Island; Craig Robinson; Patrick Sutcliffe, both of Redmond, all of WA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/306,643

(22) Filed: May 6, 1999

Related U.S. Application Data
(60) Provisional application No. 60/084,510, filed on May 6, 1998.

(51) Int. Cl.$^7$ ............................................. A61B 8/02
(52) U.S. Cl. ............................................. 600/454; 128/916
(58) Field of Search ................................ 600/440, 441, 600/443, 447, 454, 456; 73/625, 626; 128/916

(56) References Cited

U.S. PATENT DOCUMENTS 5,720,291 * 2/1998 Schwartz .............................. 600/456
5,860,924 * 1/1999 Quistgaard ........................... 600/441

* cited by examiner

Primary Examiner—Marvin M. Lateef
Assistant Examiner—Ali M. Imam

(57) ABSTRACT

An ultrasound imaging system produces three-dimensional tissue/flow images by first computing a plurality of separate two-dimensional tissue images and two-dimensional flow images. Separate tissue and flow volumes are created by applying the tissue and flow images to a three-dimensional construction algorithm. Each of the separate tissue and flow volumes is analyzed using a three-dimensional rendering algorithm to produce a rendered tissue and flow image. The separately rendered tissue and flow images are combined to produce the combined tissue/flow image. In addition, the present invention provides visual cues that allow a user to create more even scans. The invention also includes a method for correcting for probe movement. The invention also produces an image that is calculated from the partial volume data as it is being created to give a user feedback on the quality of the image they are producing. Finally, the invention compensates for variations in the cardiac cycle when selecting data to be used in creating a flow volume.

9 Claims, 7 Drawing Sheets

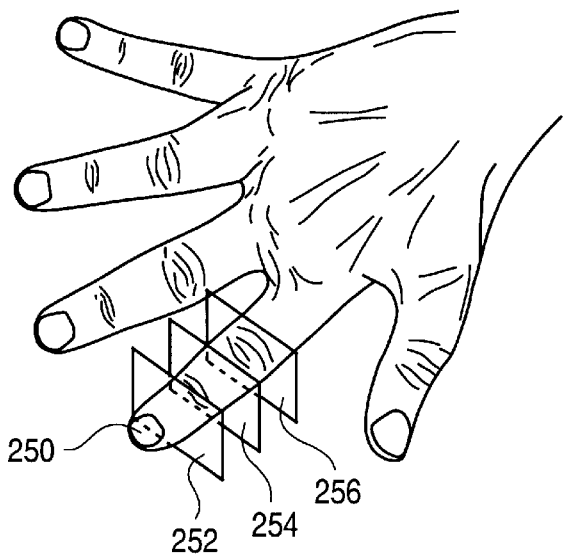
FIG. 7
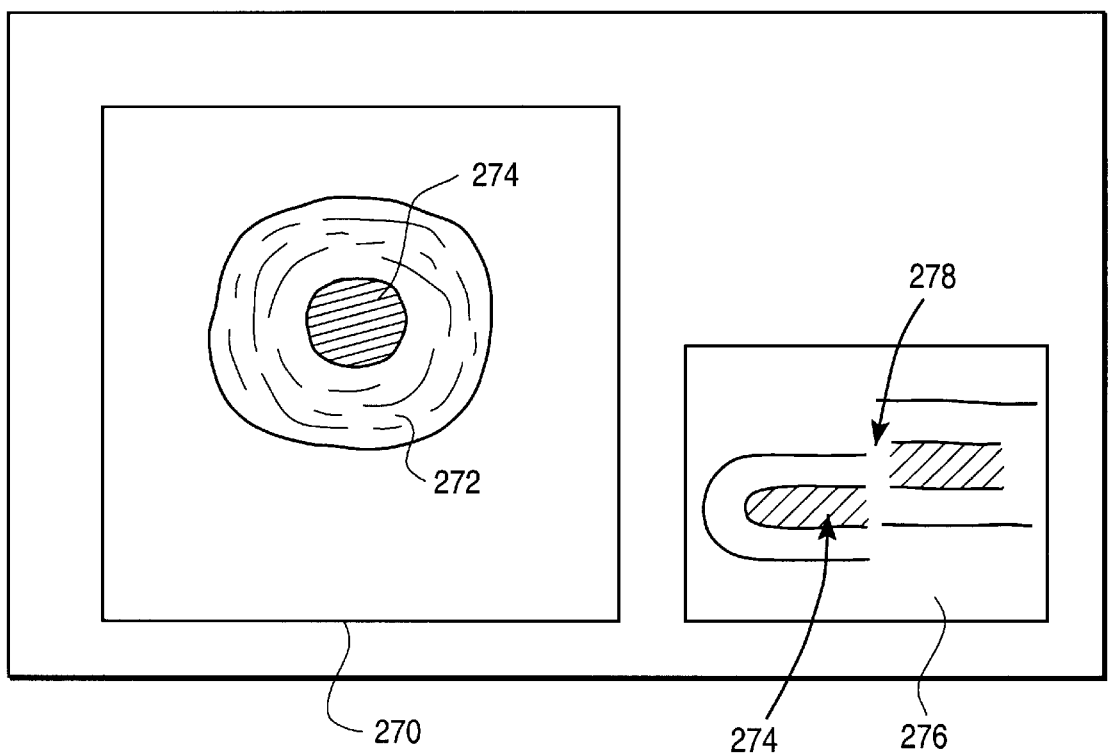

THREE-DIMENSIONAL TISSUE/FLOW ULTRASOUND IMAGING SYSTEM

RELATED APPLICATION

This application is related to U.S. Provisional Patent Application No. 60/084,510 filed May 6, 1998, the benefit of the filing date being claimed under 35 U.S.C. §119(e).

FIELD OF THE INVENTION

The present invention relates to ultrasound imaging systems in general, and in particular to ultrasound systems for producing three-dimensional tissue/flow images.

BACKGROUND OF THE INVENTION

As the processing power of microprocessors and digital signal processors increases, it has now become possible to produce substantially real-time three-dimensional images of a patient's tissue and moving blood flow using non-invasive ultrasound. With a three-dimensional image, a physician or sonographer is able to more accurately detect diseases or abnormalities in the patient.

The traditional method of producing a three-dimensional image, involves obtaining ultrasound data representative of echo intensity and Doppler shift from a number of planes in the body. A series of images containing both tissue and flow data is created and stored in memory. A three-dimensional reconstruction algorithm then analyzes the combined data in the series of tissue/flow images to create a set three-dimensional data, called a volume, that represents the tissue and blood flow in the patient. Because the reconstruction algorithm is applied to both combined tissue and flow data, tissue structure or flow deep within the image is often obscured when a rendering or two-dimensional representation of the volume data is produced. While this artifact can be reduced by decreasing the opacity curves used to render the data, this has the effect of decreasing the dynamic range of the image whereby faint tissue or flow cannot be seen.

Other problems associated with prior techniques of producing three-dimensional ultrasound images include compensating for the movement of the ultrasound transducer between each of the two-dimensional images used to create volume. Such movement can result in a rendered image looking jagged or blotchy. In addition, there are no mechanisms to alert a sonographer to the quality of a three-dimensional image they are creating prior to its final completion. Therefore, a user must wait until a scan is completed before seeing the results, and must repeat the entire scan if there is a problem.

Given the above problems associated with traditional methods of producing three-dimensional tissue/flow images, there is a need for an ultrasound imaging system that can produce three-dimensional tissue/flow images wherein data is not lost as a result of the rendering process and the quality of resulting images is improved.

SUMMARY OF THE INVENTION

To improve the quality of three-dimensional ultrasound images, the present invention comprises a method of producing three-dimensional ultrasound images by creating a series of separate two-dimensional tissue and flow images. The data in each of the two-dimensional tissue and flow images are separately analyzed to produce a volume of the tissue data and a volume of the flow data. Separate renderings of the tissue volume and flow volume are created and combined in a predetermined or user selected proportion.

In addition, the present invention also improves the appearance of a combined tissue/flow rendering by locating and filtering the edge of a flow rendering prior to combining it with a tissue rendering in order to produce a smooth transition between the tissue and flow renderings.

The present invention also includes a reduced size memory to determine the particular red, green, and blue color values used to display the combined tissue/flow rendering. The memory maps different intensity values of the tissue rendering to the same red, green, and blue color values in a manner that is determined by a histogram of pixel intensity values for the tissue rendering.

A further aspect of the present invention includes a method of aligning a series of two-dimensional images. A comparison algorithm such as a correlation function or sum absolute difference compares the pixels of one image to the pixels of a subsequent image. From the comparison, an estimate of the relative position in two directions, $\Delta X$ and $\Delta Y$ can be determined. For simplicity, each image is assumed to be taken at equal distances apart in the $\Delta Z$ direction.

The present invention also includes a visual display that allows a user to gauge where they should be in completing a scan. A user enters a rate at which they desire to move the ultrasound transducer in either mm/sec for a linear scan or degrees/sec for a rocked or rotational scan. In addition, a user enters the total length of the scan in cm or in degrees. The ultrasound system therefore computes the total duration of the scan and a visual display is created that shows how much time has passed since the beginning of a scan, compared to its computed duration.

In addition, the present invention creates and displays a partial image that is created from the tissue and flow volumes as they are being completed in order to alert a user to the quality of the three-dimensional data as it is being created. The partial image is shown simultaneously with the real-time two-dimensional images on a display screen. Finally, the present invention improves the selection of flow data during different portions of a cardiac cycle. To avoid selecting data from a two-dimensional flow image that may be misleading, the present invention selects the largest flow data from a series of two-dimensional images for use in creating a flow volume provided that the images are obtained from nearly the same position in the body.

BRIEF DESCRIPTION OF THE DRAWINGS

FIG. 7 illustrates an image that is created from a partial tissue/flow volume to provide a user with feedback about the quality of a three-dimensional scan prior to its completion.

DETAILED DESCRIPTION OF THE PREFERRED EMBODIMENT

As indicated above, the present invention is a system for improving the quality of three-dimensional tissue/flow ultrasound images.

Figure 1:
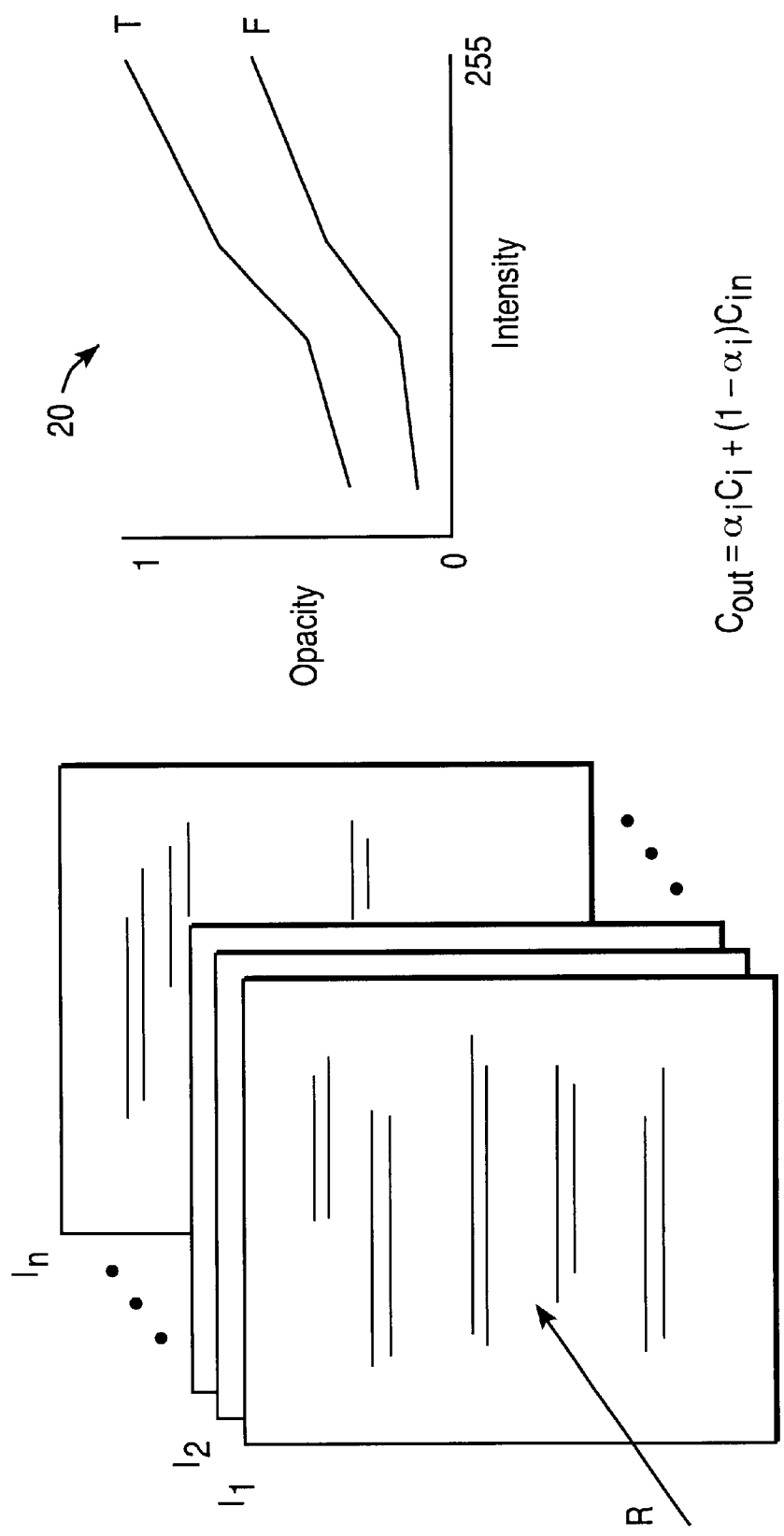
FIG. 1 illustrates a method of producing renderings of three-dimensional tissue/flow data according to the prior art.

FIG. 1 illustrates the conventional method by which three-dimensional tissue/flow ultrasound images are produced. To produce an ultrasound image in which both tissue and moving blood flow are simultaneously visible with moving blood, most conventional ultrasound systems obtain a plurality of combined two-dimensional tissue/flow images $I_1, I_2 \ldots I_n$. If these images are shown on a monitor, the tissue is generally represented as a gray scale image while the flow is shown in a color that is dependent upon flow velocity.

To produce a three-dimensional volume from the plurality of two-dimensional images, a three-dimensional reconstruction algorithm, such as that described in Ohbuchi et al., "Incremental Volume Rendering Algorithm for Interactive 3D Ultrasound Imaging", Proceedings of the 12th Int'l Conf. on Information Processing in Medical Imaging, pp. 486–500, 1991, or U.S. Pat. No. 5,787,889, is applied to the two-dimensional images. To create a two-dimensional representation of the three dimensional data, a rendering algorithm such as that described in M. Levoy, "Display of Surfaces from Volume Data", IEEE Computer Graphics Applications, Vol. 8:29–37, 1988, or multiplaner reformatting (MPR) is used. With this rendering algorithm, an imaginary light ray is directed into the ultrasound image for each pixel in the three-dimensional image to be created. The intensity of the pixel is dependent upon the opacity of the data at each corresponding location in each of the ultrasound images.

A standard step in producing two-dimensional representations of three-dimensional data sets is to determine the set of voxels that contribute to the intensity of each pixel in the final two dimensional images. Let $\alpha_i$ and $C_i$ be the opacity and intensity assigned to the voxel $V_i$. The intensity $C_{out}$ of the ray as it leaves the voxel $V_i$ is related to the intensity $C_{in}$, according to the equation.

$$C_{out}=\alpha_i C_i+(1-\alpha_i)C_{in} \quad (1)$$

where $C_i$ is the intensity of the light with diffuse and specular reflections from the surface $V_i$. The intensity to be assigned to the pixel under consideration is determined then starting from $V_n$ working towards $V_1$ taking $C_{out}$ of $V_i$ to be $C_{in}$ for $V_{i-1}$.

The values for $\alpha$ in Equation 1 are generally determined from an opacity curve that relates an intensity value for tissue and flow data to an opacity number that lies between 0 and 1. A representative opacity curve 20 is shown in FIG. 1. As can be seen, there are separate opacity curves for tissue and for flow data. In general, it is very difficult to design the opacity curves in a manner that will separate tissue from flow data so that all the structure in an image will be visible. For example, if moving blood flow is to be seen through a section of tissue, then the opacity for the tissue in front of the flow must be less than the opacity of the flow data at that point. However, if the tissue opacity is low, then any tissue structure behind the flow becomes obscured. The result of producing a three-dimensional ultrasound image from combined tissue/flow two-dimensional images often results in portions of the image being obscured.

To improve the quality of three-dimensional tissue/flow images, the present invention created separates the tissue and flow data in order to create separate rendered tissue images and flow images that are combined to produce a rendered tissue/flow image for a viewer.

Figure 2:
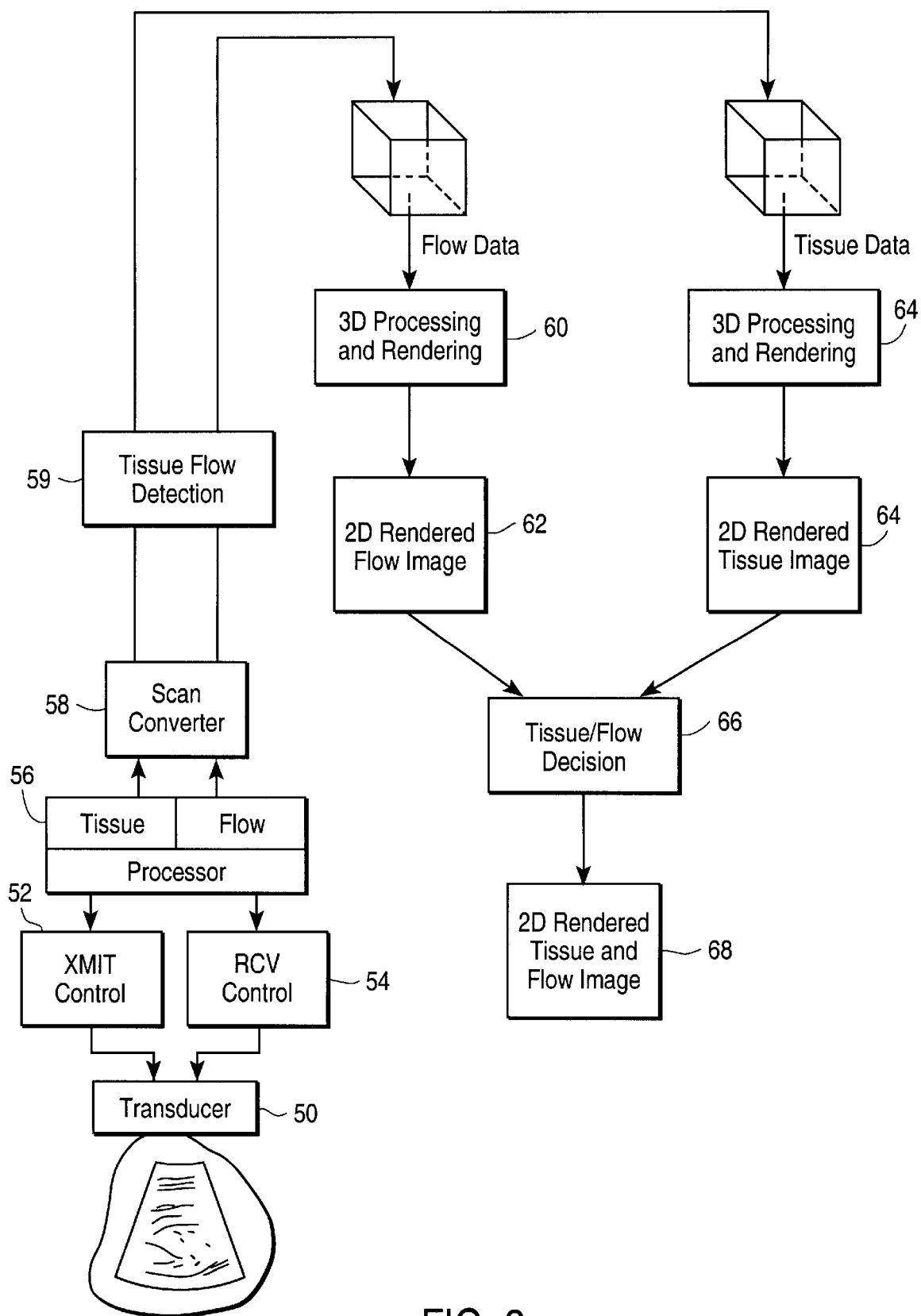
FIG. 2 is a block diagram of an ultrasound system for producing renderings of three-dimensional tissue/flow data according to the present invention.

A block diagram of a first embodiment of the present invention is shown in FIG. 2. A transducer 50 directs ultrasound signals into the patient and receives echoes from the tissue and/or moving blood flow. A transmit control device 52 applies driving signals to each of the individual piezoelectric elements of the transducer to produce a transmit beam that is directed along a particular transmit beam line within the patient. Electronic signals are produced by the individual piezoelectric elements of the transducer 50 in response to received echo signals and are applied to a receive control device or beam former 54 that calculates the echo intensity at each point along one or more receive beam lines. In the presently preferred embodiment of the invention, the transmit control 52 generates driving signals that are optimized to produce image or "B-mode" data followed by driving signals that are optimized to produce flow data. Therefore, the beam former 54 alternately produces tissue data and flow data from the echo signals received from the patient. Data from the beamformer 54 are applied to a tissue/flow processor 56 which calculates the echo amplitude for B-mode images and flow data for flow images.

The tissue data and flow data produced in the tissue/flow processor 56 remain separated and are applied to a scan converter 58 which performs a coordinate conversion such that the data can be viewed on a rectangular video monitor. The outputs of the scan converter 58 are applied to a tissue/flow detector 59 which calculates a flow rate for display in color or power mode imaging. The details of the beamformer 54 tissue/flow processor 56, scan converter 58 and tissue flow detector 59 are considered well known to those of ordinary skill in the art and therefore need not be discussed further except as they relate to the present invention.

The tissue and flow data produced by the tissue/flow detector are applied to separate flow data and tissue data processing paths. The flow data are applied to a processor or digital signal processor 60 which aligns the images and applies a three-dimensional reconstruction algorithm that creates a three-dimensional volume of the flow data. From the three-dimensional flow volume, a rendering algorithm creates a two-dimensional image 62 of the volume flow.

In the tissue data processing path, the sequence of two-dimensional B-mode images are applied to a processor or digital signal processor 64 which aligns the images and applies a three-dimensional reconstruction algorithm 64 that creates a three-dimensional volume of the tissue data. A two-dimensional image 64 of the three-dimensional tissue volume is produced by a rendering algorithm.

At this point, a user can view either a two-dimensional image 62 of the flow volume or the two-dimensional image 64 of the tissue volume. By creating separate images 62 and 64, different rendering algorithms can be applied to the flow volume data or the tissue volume data. In addition, because the transmit control 52 generates alternate tissue and flow data during a single scan, the resulting tissue and flow data are closely aligned with respect to each other.

To produce a combined rendered tissue/flow image 68, each pixel in the rendered flow image 62 and the rendered tissue image 64 is applied to a tissue/flow decision algorithm 66 which determines whether a pixel and the combined image should be shown as tissue or flow. The tissue/flow algorithm is preferably a threshold value that determines if the flow pixel in the image 62 is greater than some predefined value, then the corresponding pixel in the combined image 68 is shown as flow, otherwise, a pixel from the tissue image 64 is used. The results of the tissue/flow decision algorithm 66 produces the rendered tissue/flow image 68.

The architecture shown in FIG. 2 has numerous advantages over the prior art mechanisms of producing three-dimensional ultrasound images from combined tissue/flow data. First, a user can view a rendered tissue image 64, flow image 62 or combined tissue/flow image 68 that are all obtained using a single scan with an ultrasound transducer. Additionally, different algorithms can be used to analyze the tissue and flow data in order to optimize the results obtained for each data type. Finally, deep data in the tissue or flow images is not lost during processing.

Figure 3:
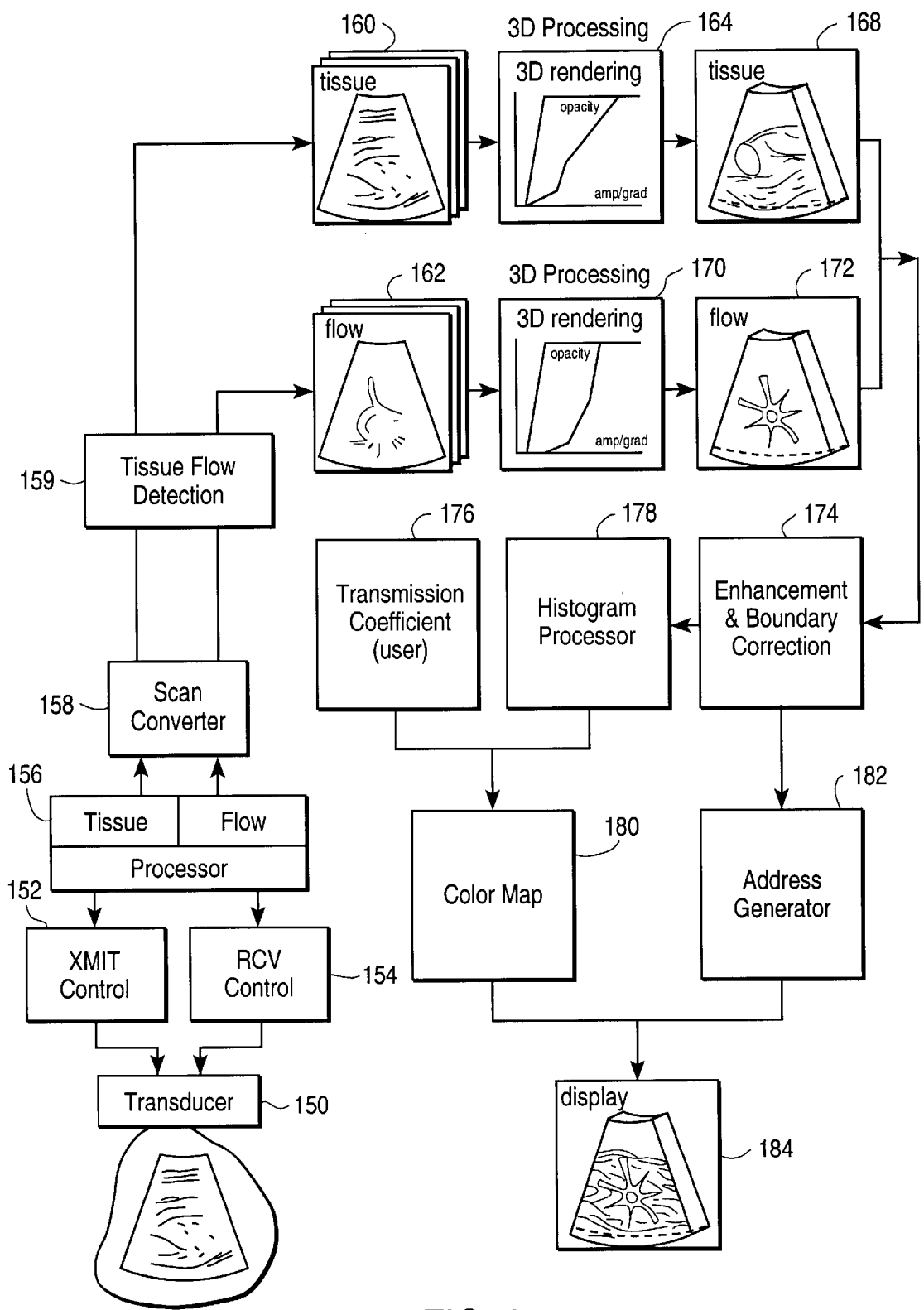
FIG. 3 is a block diagram of an ultrasound system for producing renderings of three-dimensional tissue/flow data according to an alternate embodiment of the present invention.

An alternate embodiment of the invention is shown in FIG. 3, the ultrasound imaging system includes a transducer 150 that directs ultrasound signals into the patient and receives echoes from the tissue and/or moving blood flow. A transmit control device 152 applies driving signals to the individual piezoelectric elements of the transducer to produce ultrasonic energy at a desired time such that a transmit beam of energy is directed along a particular transmit beam line. Electronic signals are produced by the individual elements of the transducer 150 in response to the received echoes. The electronic signals are supplied to a receive control device or beam former 154 that amplifies and digitizes the received electronic echo signals for further processing. The received echo signals are then supplied to a tissue/flow processor 156 that combines the echo signals from the various transducer elements in order to determine an echo intensity and a Doppler shift at a number of points along a number of receive beam lines.

The tissue/flow processor 156 separates the echo signal data received in response to tissue or B-mode imaging and the echo signal data created in response to Doppler imaging. The data from each type of imaging is supplied to a scan converter 158 that performs a coordinate transformation in order to produce sets of image data that can be displayed on a video monitor. The outputs of the scan converter 158 are applied to a tissue/flow detector 159 that calculates flow values for color or power mode imaging.

To produce a three-dimensional tissue/flow image, a set of N two-dimensional tissue images 160 and a set of N two-dimensional flow images 162 are created and stored in a memory within the ultrasound system where they are applied to a three-dimensional processing and rendering algorithm 164. The data for each of the two-dimensional tissue images 160 are analyzed using a three-dimensional reconstruction algorithm in order to create a tissue volume. The tissue volume data are then applied to rendering algorithm, whereby the intensity of any pixel image is determined using an opacity curve that is constructed for tissue data only. In a presently preferred embodiment of the invention, the opacity selected for any given pixel is determined by a curve that relates opacity to intensity as well as a curve that relates opacity to the gradient in intensity values. The actual opacity selected is the product of the opacity determined by intensity and the opacity selected by gradient. Such intensity/gradient opacity curves are considered well-known to those of ordinary skill in the ultrasound imaging art. From the opacity curve and the rendering algorithm, a rendering 168 of the three-dimensional tissue volume data is created.

Similar processing steps take place on the data for the N two-dimensional flow images 162. The two-dimensional image data is applied to a three-dimensional processing and rendering algorithm 170. A three-dimensional reconstruction algorithm is applied to the N sets of flow data in order to create a flow volume. The flow volume data is then applied to a rendering algorithm that utilizes an intensity/gradient opacity curve that is selected for flow data only. The result is a rendering 172 of the flow volume data.

To produce a rendered tissue/flow image, the rendered tissue image 168 and the rendered flow image 172 are linearly combined according to the equation:

$$I_{t/f} = \beta I_t + (1-\beta) I_f \qquad (2)$$

wherein $I_{t/f}$ is the combined rendered tissue/flow image, $I_t$ is the rendered tissue image 168, $I_f$ is the rendered flow image 172, and $\beta$ is a variable having a value between 0 and 1 that is determined by a user of the ultrasound system. The tissue portion of the combined image is preferably a gray scale image while the flow portion of the image is displayed in a color that is dependent on flow velocity.

Before the rendered tissue image 168 and rendered flow image 172 are combined, a boundary correction algorithm, represented by the block 174, is employed to determine the boundary of the rendered flow image 172. This is preferably performed by searching for the pixels in the rendered flow image 172 that are adjacent pixels having zero intensity. To improve the quality of the combined tissue/flow image, the pixel values at the boundary of the rendered flow image 172 are averaged with adjacent pixels in the corresponding rendered tissue image 168 in order to provide a smooth transition between the flow and tissue portions of the combined tissue/flow image 184.

The coefficient $\beta$ in Equation 2 is received from a user at a block 176. The coefficient determines the relative intensity of the rendered tissue image 168 with respect to the rendered flow image 172. For each value of $\beta$ received, the particular red, green, and blue color values that define a color of a particular pixel in the combined image must be determined. For an 8-bit ultrasound system, there are 256 possible intensity values for each pixel in the rendered tissue and flow images 168 and 172. Because each pixel is represented by an 8-bit red, green, and blue color value, a color map storing all possible pixel combinations would occupy approximately 192 kilobytes. In an ultrasound machine where memory is scarce, this map may be unnecessarily large.

Figure 4:
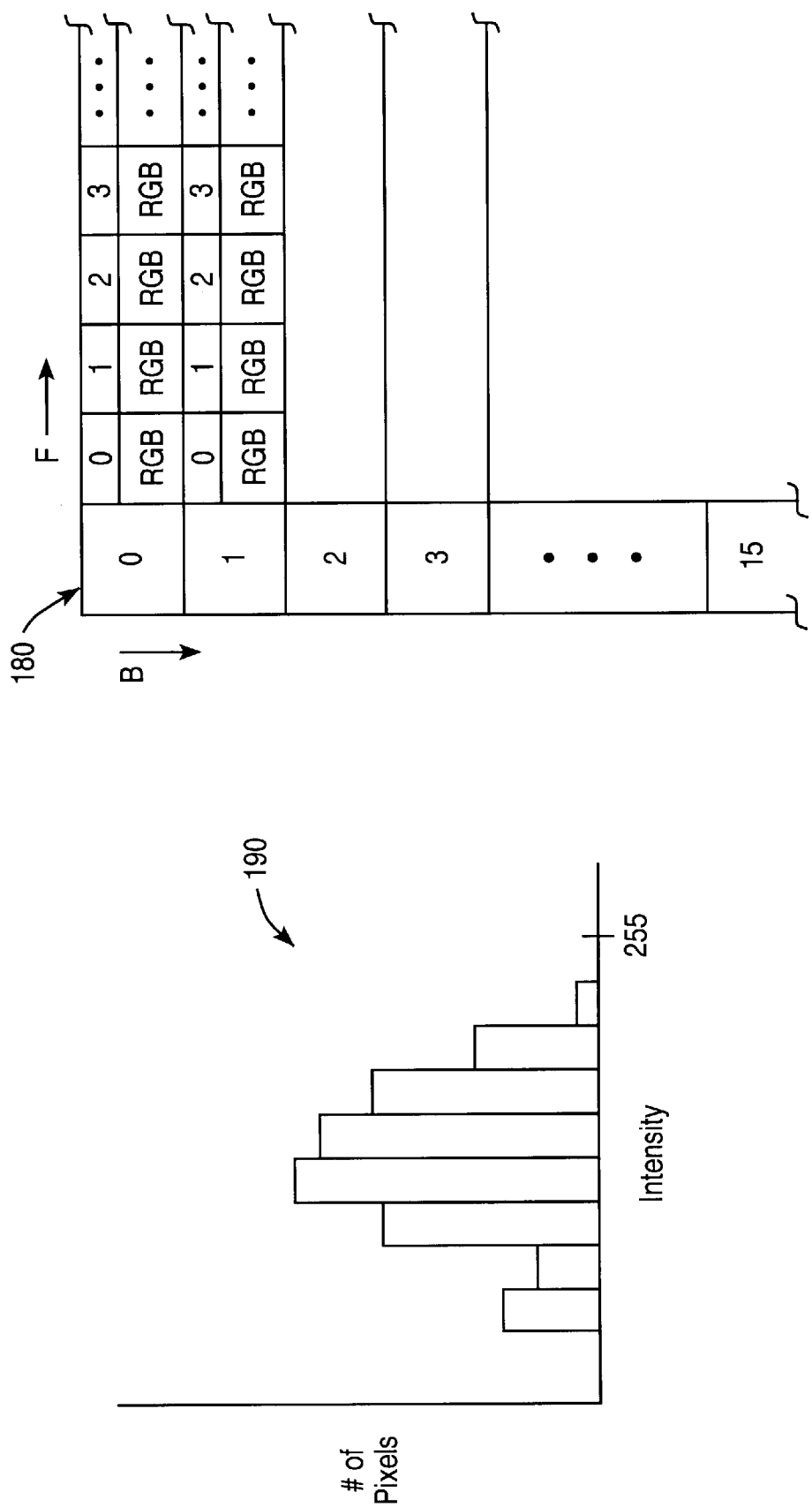
FIG. 4 illustrates the structure of a table used to store a reduced set of pixel color values according to another aspect of the present invention.

To reduce the size of the color map required, the present invention utilizes a diminished color map 180 as shown in FIG. 4. In the presently preferred embodiment of the invention, the color map contains 16 rows and 256 columns. Each possible tissue intensity value is mapped to, or is binned in, one of the 16 rows, wherein different red, green, and blue color values are stored in the table for each of the 256 possible flow values. The mapping of the tissue intensity values to a particular row in the color map is determined by analyzing a histogram of pixel intensity values in the rendered tissue image 168. A histogram processor 178 (FIG. 3) produces a histogram 190 (as shown in FIG. 4) that defines the distribution of pixels having a particular intensity value within the image. In the presently preferred embodiment of the invention, the number of rows in the color map is 16. If the histogram of tissue intensity values is evenly distributed, then each row of the color map will map to approximately 256/16 intensity values. For example, tissue data values 0 to 15 map to row 0, tissue values 16 to 31 map to row 1, etc. However, if the histogram is not evenly distributed, the pixel intensity values having the most number of pixels may be more finely divided in the color map in order to improve the dynamic range of the image.

To compute the red, green, and blue color values that define the color of a pixel in the combined tissue/flow image 184, an address generator 182 produces an address of each pixel in the combined image. The tissue intensity value for that pixel is mapped to one of the 16 rows in the color map 180, and the flow intensity value for the corresponding location in the rendered flow image 172 is determined. From this, the color map 180 provides the correct red, green, and blue color values for the pixel in the combined three-dimensional tissue/flow image 184. It will be appreciated that the particular red, green, and blue color values stored in the color map 180 are computed according to Equation 2 depend upon the transmission coefficient $\beta$ that is received from a user at the block 176. The particular value of $\beta$ may be entered using a knob or other control on the ultrasound machine's control panel or by using a software control. As a new value of $\beta$ is received, the RGB data within the color map is recalculated.

As indicated above, in order to produce a combined rendered tissue/flow image with the present invention, it is preferable that the data for the tissue image be obtained almost simultaneously with the data for the flow image. This is achieved by alternating performing B-mode and Doppler mode scans. In addition, the rendered tissue and flow images should be calculated using the same lighting conditions.

Figure 5A:
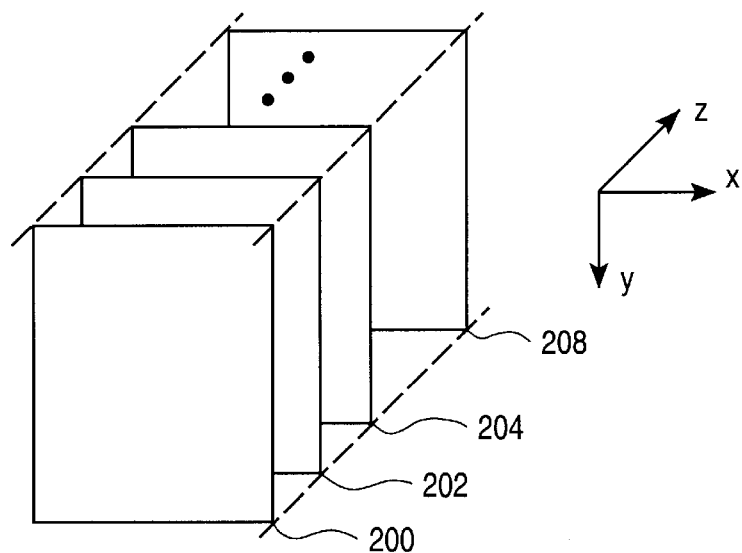
FIGS. 5A–5B illustrate the displacement of two-dimensional images that can occur with transducer movement.
Figure 5B:
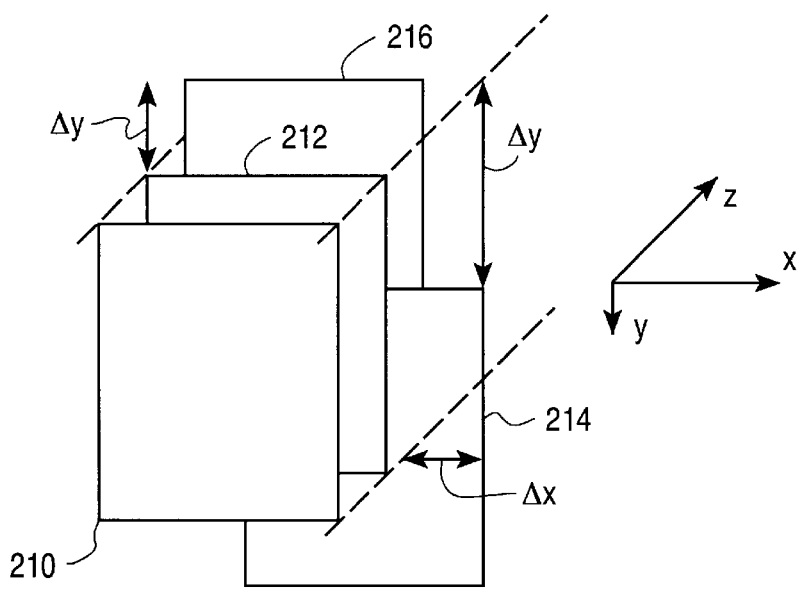

To produce the best possible set of ultrasound volume data, it is preferable that each of the two-dimensional images used to create the volume data be aligned. FIG. 5A illustrates a number of two-dimensional tissue or flow images 200, 202, 204 . . . 208. Each of these images is substantially aligned in the X- and Y-direction. In addition, the relative spacing between the images in the Z-direction (which corresponds to the time between images) is substantially constant. In practice, however, the two dimensional ultrasound images are often not aligned. FIG. 5B illustrates a series of images 210, 212, 214, 216 that are offset in the $\Delta X$ and $\Delta Y$ directions. Such offsets may be due to movements of the transducer by the sonographer or due to movement of the body by breathing or the cardiac cycle. In addition, the spacing between the images in the Z-direction may not be the same if the probe used to acquire the images is not moved at a constant speed.

In order to create three-dimensional volume data from the images 210–216, it is necessary to align the data in each of the images. To align the images, an estimation must be made of the relative movement in the $\Delta X$, $\Delta Y$ direction. In the presently preferred embodiment of the invention, it is assumed that the probe is moved at a constant rate and the distance $\Delta Z$ between each of the images is substantially constant. To compute the distances $\Delta X$ and $\Delta Y$, the pixels in each of the images can be analyzed to determine where a feature in one image is located with respect to the position of the feature in a subsequent image. The comparison may be done using a Sum Absolute Difference (SAD) technique wherein images are divided into groups of pixels. Corresponding groups of pixels in each image are subtracted and the result is summed. The two groups having the most similarity will produce the smallest sum and therefore can be considered to contain the same pattern. Next, the relative position of each group that produced the smallest sum is determined and the data in the subsequent image can be realigned based on the relative position. Alternatively, a two-dimensional correlation can be performed on the data in sequential images. The correlation function will produce a maximum that indicates the relative offset in the $\Delta X$ and $\Delta Y$ direction between the two images. Similar techniques can be applied to rocked or rotational scans. In those cases, it is preferable to assume that the rate of rotation or rocking is always constant.

Figure 6:
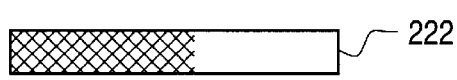
FIG. 6 illustrates a number of indicators that provide a guide for a user to complete a linear or rocked scan.
Figure 6:
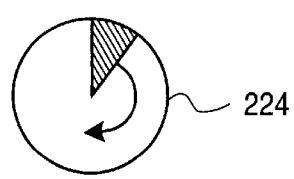
Figure 6:
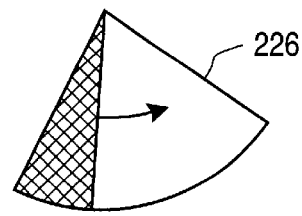

To aid the user in maintaining a constant probe speed when performing a linear, rocked or rotational scan, the present invention also provides an indicator on a video monitor of the ultrasound system. Examples of indicators shown in FIG. 6 include a series of counting numbers 220, a progress bar 222 or a sweeping clock hand 224. The rate at which the indicator is activated is dependent upon how fast the user indicates they wish to move the probe. For example, the user may wish to move the probe along a linear line at 2.5, 5, or 10 millimeters per second. In addition, the user enters the length of the scan they wish to produce. The ultrasound system therefore divides the length of the scan by the speed of the transducer to determine the total duration of the scan. For example, the user may enter a scan of 10 cm. and a speed of 10 mm./sec. such that the ultrasound system calculates that the scan will have a duration of 10 seconds. Therefore, upon initiation of a scan by a user pressing a button, foot switch or the like, the countdown indicator 220 would count down from 10 seconds, the progress bar 222 would fill up in 10 seconds or the clock symbol 220 would sweep around the face in 10 seconds. By viewing an indicator such as the indicators 220, 222, or 224 on the ultrasound display screen, the user has some guide to judge where the transducer should be in the scan relative to the length of the scan. This aids the sonographer in maintaining the speed of the transducer at a relatively constant rate thereby simplifying the calculations for determining probe movement in the $\Delta X$ or $\Delta Y$ direction as shown in FIG. 5B and described above. Thus, by using the indicators shown in FIG. 6, better three-dimensional ultrasound images can be obtained with a free-hand probe.

The same indicators can be used when the images are obtained by rocking the transducer rather than moving it linearly. In a rocked movement, the ultrasound transducer is not moved linearly but is swept through a predefined angle. In this embodiment, the user enters the angle in which they intend to sweep the probe and the number of degrees per second they will rock the probe. For example, a user enters a probe movement of 60° at a rate of 6° per second so that the ultrasound system calculates it will take 10 seconds to complete the sweep. Therefore, the indicators 220, 222, or 224 are used to provide visual estimate of the rate at which the rock scan should be completed. Alternatively, an indicator 226 which is an arc that fills in proportion with the calculated time required to complete the scan in order to provide a user with some guide as to how fast the probe should be moved. The indicators can also be used for a rotational scan.

In order to further provide a physician or sonographer with immediate feedback concerning the quality of a three-dimensional image being produced, the present invention also produces images created from the three-dimensional volume data as it is being received. For example, assume that a physician wishes to take an ultrasound image of a patient's finger 250 as shown in FIG. 7. As an ultrasound probe is moved along the axis of the finger, a series of two-dimensional images 252, 254, 256 are created. These images are shown live on a display as an image 270 and illustrate a cross section of the finger including a flesh portion 272 and a central bone 274. As the images 252–256 are being received, the ultrasound system is creating the three-dimensional volumetric data from the images. In order to provide a user with feedback concerning the quality of the three-dimensional data being received, the ultrasound system displays a partial two-dimensional rendering 276 of the three-dimensional data and displays the partial rendering 276 to the user on a portion of the screen simultaneously with the live two-dimensional image being received. The partial rendering 276 is taken in a direction that is different than the orientation of the two-dimensional images used to create the three-dimensional data. For example, the rendering 276 shows a portion of the patient's finger along an axis of the finger. If the user sees some abnormality in the image produced such as a discontinuity 278 that appears in the bone 274 of the finger, then they know that either the ultrasound transducer has been moved inappropriately or that some other processing error has occurred. Therefore, the user can restart the scan without waiting until the entire scan has been completed. The rendered image obtained from the partial volume data may include slices, volume renderings or surface renderings, etc.

Depending on the processing power available, the data used to create the image could be less than the data that would be used to produce an actual rendering or slice of the volume data in order to calculate the partial rendering from the partial volume data in substantially real-time.

To produce the partial rendering, all incoming images are processed to determine their position by the $\Delta X$, $\Delta Y$ and $\Delta Z$ mechanism described above, or via the method described in U.S. Pat. No. 5,876,342 or via position sensors. Once the incoming image is associated with a position comprising X, Y, Z in mm or the angles $\Theta X$, $\Theta Y$, $\Theta Z$ for orientation, the image is applied to an incremental to the incremental reconstruction algorithm such as that described in the Ohbuchi article mentioned above. At that point, the information contained in the image is put in the volume according to its physical location in space. The ultrasound system keeps track of the position of all the planes being acquired, including the first and the last plane added to the volume, a rendering method such as Multi-Planar Reformatting (MPR) is applied between those bounds. To display this partially rendered image on the screen, a space is allocated. The space allocated may become smaller than the rendered image during the course of the three-dimensional acquisition. In that case, when the rendered image reaches 75% of the space allocated the system only renders the portion of the volume that will fill the 75% of the image buffer starting from the last image acquired (i.e., the oldest part of the volume is not rendered anymore), giving to the user an impression of image scrolling. This method saves space on the screen and allows the display of both the regular two-dimensional ultrasound image and an image rendered from the volume, giving the user a complete real-time feedback for the three-dimensional scan being performed.

Figure 8:
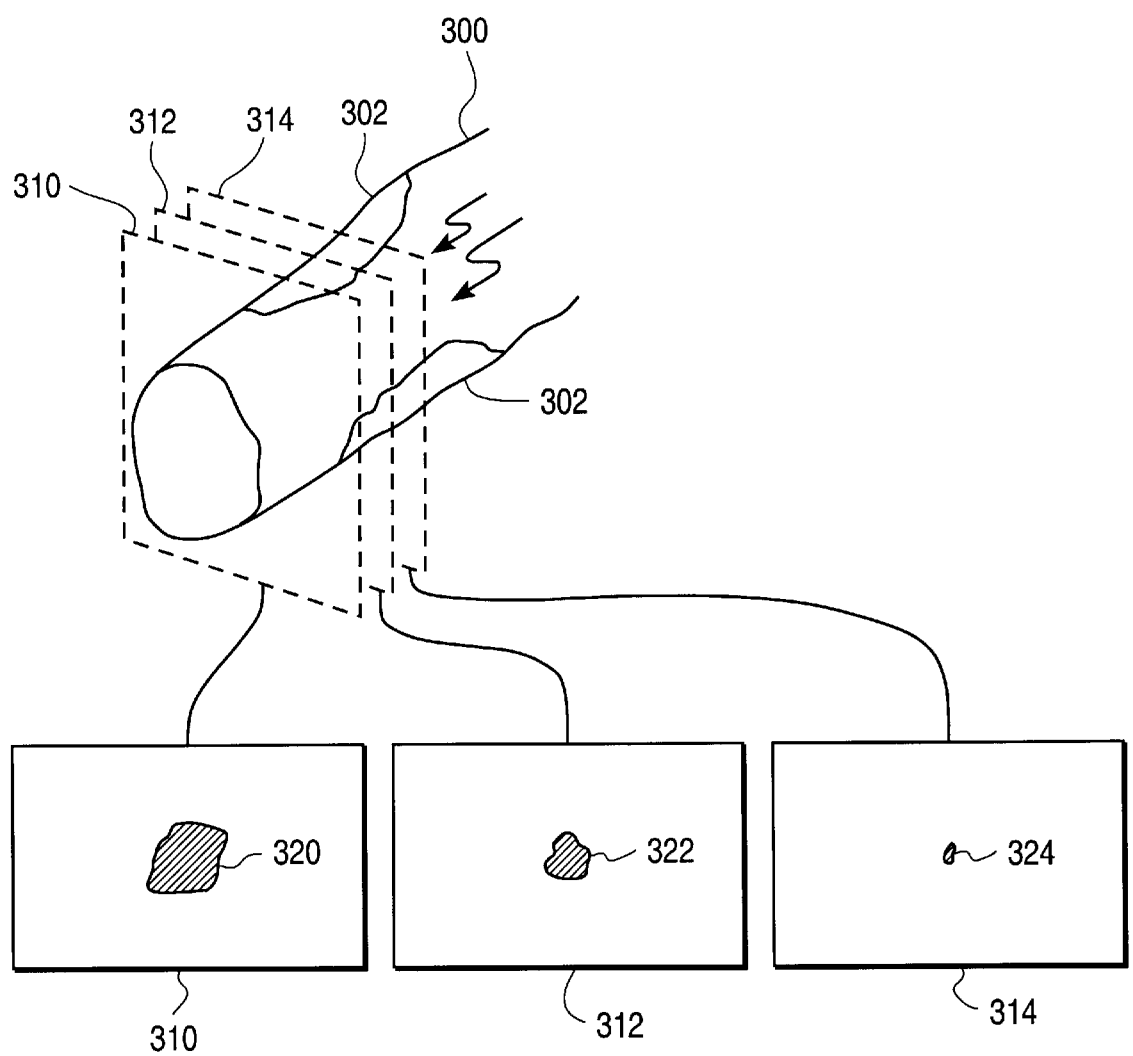
FIG. 8 illustrates a method of compensating for flow variations that occur with a cardiac cycle when creating flow volumes without having to perform cardiac gating according to another aspect of the present invention.

FIG. 8 shows yet another aspect of the present invention that operates to improve the quality of three-dimensional ultrasound images. In many instances, ultrasound imaging is used to evaluate the degree of blood flow through a vessel. FIG. 8 shows a vessel 300 having a blockage 302 that limits the passage of blood through the vessel. A series of two-dimensional flow images 310, 312, 314 are taken across the blockage in order to determine the extent to which blood flow is reduced. As will be appreciated, the extent of blood flow at any given time in a vessel depends not only on the health of the vessel but also on the time at which the images were taken relative to the cardiac cycle. When the heart is pumping blood, the flow through the vessel will be greater than the time at which the heart is resting. If the frame rate at which the images used to create the three-dimensional volume data provides more data than is required to compute the flow volume then data is discarded. However, it would not be possible to know whether the flow rate determined in any individual image was due to reduced flow capacity in the vessel or whether the image happened to be acquired during a low velocity point in the cardiac cycle.

To overcome this problem without the user of electrodes on the patient and cardiac gating, the present invention analyzes the flow data in each of a series of sequential images and selects the largest flow data for use in constructing flow volume. In the example shown in FIG. 8, the image 310 contains a flow 320 which is larger than the flow 322 shown in image 312 and is still larger than the flow 324 shown in the image 314. If the image 312 were selected for use in constructing the flow volume, it may appear to a sonographer that the flow is reduced when in fact the image 312 may have been taken during relatively low velocity point in the cardiac cycle.

The images are associated with a spatial position via the $\Delta X$, $\Delta Y$ and constant $\Delta Z$ method described above or in the method described in U.S. Pat. No. 5,876,342 or via a position sensor device. Then the systems checks the resolution of the final volume, i.e., what is the size in mm of the voxel. If the distance $\Delta Z$ between the candidate images is such that those images would be mapped to the same voxels in the volume, then the images are aligned (i.e., $\Delta X$ and $\Delta Y$) and the maximum intensity of the images is kept therefore creating a new image. This new image is then sent to the three-dimensional reconstruction algorithm to be added to the volume. Alternatively, the method can just keep the image (between the candidates) which has the highest mean (indicating that there is more flow then in the other candidates) and send the image with the highest mean to the reconstruction algorithm to be added to the volume.

An alternative method to improve the acquisition of flow data in a volume is to use all the images that the system gets, associate them with a position (with methods described previously), and then use an alternate volume reconstruction. The alternative reconstruction can be called a "reverse mapping process" where, for each voxel in the volume, the ultrasound systems looks in the acquired images for the pixels which can contribute to the value of the voxel (because of proximity which is function of the volume sampling or voxel size). Then, instead of having all those pixel candidates contributing to the voxel value via an interpolation process (where the weight of the contribution is based on the distance to the voxel), the system picks the candidate that has the maximum intensity value and assigns this value to the voxel. An other alternate reconstruction is a "forward mapping" where all the pixels in the images are mapped to the volume. If several pixels map to the same voxel in the volume, then the following rule applies: the voxel value is replaced by a new pixel value only if the new pixel has a higher intensity than the voxel.

As can be seen from the above, the present invention is a number of techniques that improve the quality of three-dimensional ultrasound images.

The embodiments of the invention in which an exclusive property or privilege is claimed are defined as follows:

1. A method of producing three-dimensional tissue and flow ultrasound images, comprising:

storing data for a number of two-dimensional tissue images;

analyzing the data for the number of two-dimensional tissue images to produce data for a three-dimensional tissue image;

storing data for a number of two-dimensional flow images;

analyzing data for the number of two-dimensional flow images to produce data for a three-dimensional flow image;

producing a rendered tissue image of the three-dimensional tissue data and a rendered flow image of the three-dimensional flow data; and combining the rendered tissue image and the rendered flow image to create a rendered tissue and flow image.

2. The method of claim 1, wherein the data for the three-dimensional tissue image is combined with the data for the three-dimensional flow image in an amount that is selectable.

3. The method of claim 1, further comprising:

smoothing a boundary of the data for the three-dimensional flow image as the data is combined with the data for the three-dimensional tissue image.

4. The method of claim 3, wherein the boundary of the three-dimensional flow image is smoothed by searching for pixel data that are adjacent to pixel data having zero values and replacing the zero value data with an average of the pixel data at a corresponding location in the three-dimensional tissue image and the three-dimensional flow image.

5. The method of claim 1, wherein the data for the number of two-dimensional tissue and flow images is analyzed with a volumetric rendering algorithm.

6. A method of producing three-dimensional flow data for use in the method of producing three-dimensional tissue and flow ultrasound images of claim 1, comprising:

generating a number of two-dimensional flow images;

analyzing flow data in the number of two-dimensional flow images that are taken in substantially the same position to determine which image has the greatest flow data, selecting the image having the greatest flow data for use in creating the three-dimensional flow data.

7. The method of claim 1, further comprising:

aligning the two-dimensional tissue and flow image before rendering.

8. An ultrasound system, comprising:

a transducer for directing ultrasound energy into a patient and receiving echo signals from the patient;

a tissue/flow processor for receiving the echo signals and determining a magnitude and Doppler shift of the received echo signals;

a memory in which the data required to create a number of two-dimensional tissue images and a number of two-dimensional flow images is stored;

a processor that analyzes the data for the number of two-dimensional tissue and flow images and creates three-dimensional tissue and flow data, and a rendered tissue image from the three-dimensional tissue data and a rendered flow image from the three-dimensional flow data;

a control that receives a proportion constant from a user having a value that is selectable between 0 and 1; and wherein the rendered tissue image is combined with the rendered flow image in a ratio determined by the proportion constant received from the user.

9. The ultrasound system of claim 8, wherein the processor smoothes the data of a boundary of the three-dimensional flow image and the data for the three-dimensional tissue image.

* * * * *